United States Patent [19]

Musacchio et al.

[11] Patent Number: 4,898,860

[45] Date of Patent: Feb. 6, 1990

[54] ANTICONVULSANT COMPOSITION AND METHOD

[75] Inventors: Jose M. Musacchio, New York, N.Y.; Frank C. Tortella, Columbia, Md.

[73] Assignee: New York University, New York, N.Y.

[21] Appl. No.: 174,175

[22] Filed: Mar. 28, 1988

Related U.S. Application Data

[63] Continuation-in-part of Ser. No. 897,410, Aug. 18, 1986, abandoned, which is a continuation-in-part of Ser. No. 766,838, Aug. 16, 1985, Pat. No. 4,694,010.

[51] Int. Cl.$^4$ .................. A61K 31/44; A61K 31/55; A61K 31/415
[52] U.S. Cl. .................................. 514/215; 514/217; 514/304; 514/389
[58] Field of Search ................ 514/389, 215, 217, 304

[56] References Cited

FOREIGN PATENT DOCUMENTS 1183403 3/1970 United Kingdom .
2074026 10/1981 United Kingdom .

OTHER PUBLICATIONS

Chemical Abstracts (1984) 16449H.
High-Affinity DM Binding Sites in Guinea Pig Brain, Craviso, G. L. and Musacchio, J. M., *Mol. Pharmacol.*, 23:619–628 (1982).
High-Affinity DM Binding Sites in Guinea Pig Brain, Craviso, G. L. and Musacchio, J. M., *Mol. Pharmacol.*, 23:629–640 (1982).
Merck Index, 10th Ed., No. 6727.
Merck Index, 10th Ed., No. 1127.

*Primary Examiner*—Stanley J. Friedman
*Attorney, Agent, or Firm*—Darby & Darby

[57] ABSTRACT

An anticonvulsant composition comprising as an active ingredient an amount effective for controlling seizures in mammals of a compound selected from the group consisting of dextromethorphan and other non-narcotic, non-addictive, low-toxicity compounds that bind to the same central nervous system sites as dextromethorphan. The composition may also contain an antiepileptic hydantoin, which is potentiated by said compound.

15 Claims, 10 Drawing Sheets

ANTICONVULSANT COMPOSITION AND METHOD

This is a continuation-in-part of application Ser. No. 897,410 filed Aug. 18, 1986 now abandoned in turn a continuation-in-part of application Ser. No. 766,838, filed Aug. 16, 1985 now U.S. Pat. No. 4,694,010 issued Sept. 15, 1987. The entire disclosure is incorporated by reference.

FIELD OF THE INVENTION

This invention relates to a group of novel compositions containing diphenylhydantoin and/or dextromethorphan or another compound that binds to the same sites in the brain as dextromethorphan, with substantially the same or higher affinity. Another aspect of this invention relates to the use of these compositions as anticonvulsants, and to methods for controlling seizures using these compositions.

BACKGROUND OF THE INVENTION

Most types of epileptic seizures, including induced generalized or focal seizures, except absence seizures, can be treated and prevented with diphenylhydantion (DPH), which is also commonly called phenytoin, and other antiepileptic hydantoins.

DPH has the following structural formula:

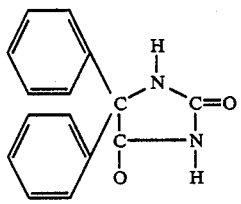

DPH usually exerts antiepileptic activity without causing general depression of the central nervous system. It can limit the development of maximal seizure activity and reduce the spread of the seizure process from an active focus.

Antiepileptic preparations containing DPH (and other antiepileptic hydantions) are available in solid (oral) and liquid (oral and injectable) forms; they contain from 30 to 250 mg of DPH per unit dose.

The effectiveness of DPH increases with dosage. However, DPH is also toxic. Most of its toxic effects increase with dosage and length of exposure, and vary with the mode of administration.

Dose-dependent toxic effects associated with chronic use of DPH and other hydantoins include cerebellar vestibular effects (nystagmus, ataxia, diplopia, vertigo, etc.) and other central nervous system disturbances (blurred vision, mydriasis, hyperactive tendon reflexes, etc.), behavioral changes (hyperactivity confusion, dullness, drowsiness and hallucinations), increased frequency of seizures, peripheral neuropathy gastrointestinal distress, gingival hyperplasia, osteomalacia, megaloblastic anemia (that can be fatal), hirsutism, endocrine effects, lymphdenopathy et al. At very high doses (especially when administered intravenously), DPH can also cause cardiovascular collapse and/or general depression of the central nervous system.

DPH is not the only antiepileptic drug. A variety of other antiepileptic agents are known. Unfortunately, many of them also have undesirable toxic and side effects. Moreover, most known antiepileptic agents are effective for only selective types of seizures.

Accordingly, there is a need in the field for development of an anticonvulsant agent that would cause as few and as mild toxic and side effects as possible and yet be effective against a wide variety of seizure types. More specifically, there is a need for an anticonvulsant agent that would be effective at doses that minimize dose-related side effects against a variety of seizures.

In Mol. Pharmacol., 23:619–628 and 23:629–640 (1983) Craviso, G. L. and Musacchio, J. M. reported that dextromethorphan (DM), a non-narcotic, nonaddictive, antitussive agent, had distinct binding sites in the central nervous system, which were different from the binding sites for opiate compounds. The same investigators found that the binding of DM was effectively inhibited in vitro by a number of non-narcotic centrally active antitussives (including certain DM analogs), certain phenothiazine neuroleptics, as well as some other compounds such as selective antidepressants, antihistamines, and muscarinic agents (i.e. agents that bind to the nuscarinic receptor). They also found that the in vitro binding of DM to the central nervous system was markedly increased in the presence of certain compounds such as DPH and noscapine, but they were unable to predict which compounds would enhance DM binding and which would not. The authors proposed that research be conducted to determine whether DPH is an antitussive (or whether DM is an anticonvulsant), but that statement is at best a proposal for experimentation and does not suggest the method or the compositions of the present invention. Specifically, the anticonvulsant activity of DM can not be deduced or suggested from the disclosure of these references. In addition, the fact that DPH increases the binding of DM does not suggest that one would potentiate activity of the other, much less that DM would potentiate DPH activity.

It has now been discovered that DM and several other compounds that bind to the same sites in the brain possess substantial anticonvulsant activity in vivo. More important, it has been unexpectedly discovered that DM and these other compounds vigorously potentiate the anticonvulsant activity of DPH in vivo when administered simultaneously (or consecutively) with DPH. As a result, the minimum effective does of DPH (and consequently its dose-dependent side-effects) can be substantially decreased. The potentiating effect is present even at subthreshold levels of DM (or the other compounds that bind to the same CNS sites).

Dextromethorphan (D-3-methoxy-N-methylmorphinan) has the following structural formula:

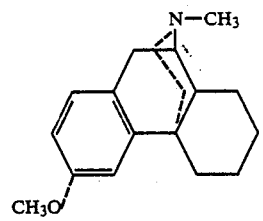

It is sold as an antitussive in various liquid, resin, and solid antitussive dosage forms containing from 5 to 30 mg/5 ml of DM (or the equivalent), together with alcohol and/or other carriers and active ingredients used in management of cough and other symptoms of the common cold.

Although DM is a potent antitussive, it has no analgesic or addictive properties. Unlike codeine to which it is structurally related, it rarely produces drowsiness or gastrointestinal disturbances and has low toxicity (Goodman & Gilman's, The pharmacological Basis of Therapeutics, Sixth Ed., MacMillan Publishing Co., New York 1980).

Therefore, use of DM (and other relatively innocuous compounds that compete with DM for the same CNS binding sites) to potentiate DPH will result in a substantial decrease in the dose-and exposure-dependent side effects of DPH with a concomitant enhancement (or without a compromise) in anti-seizure activity.

OBJECTS OF THE INVENTION

Accordingly, it is an object of this invention to provide a method for controlling seizures in mammals, and particularly clinical epileptic seizures.

Another object of this invention is to provide pharmaceutical formulations comprising an effective amount of anticonvulsant agents useful for inhibiting, preventing, or controlling epileptic seizures.

Another object of the invention is to provide pharmaceutical compositions that have anticonvulsant activity similar or superior to that of DPH, at lower doses than DPH, said compositions having substantially less toxicity and fewer side effects than DPH.

These and other objects of the invention will be apparent to one of ordinary skill in the art in light of the present description, appended claims and accompanying drawings.

SUMMARY OF THE INVENTION

Figure 1:
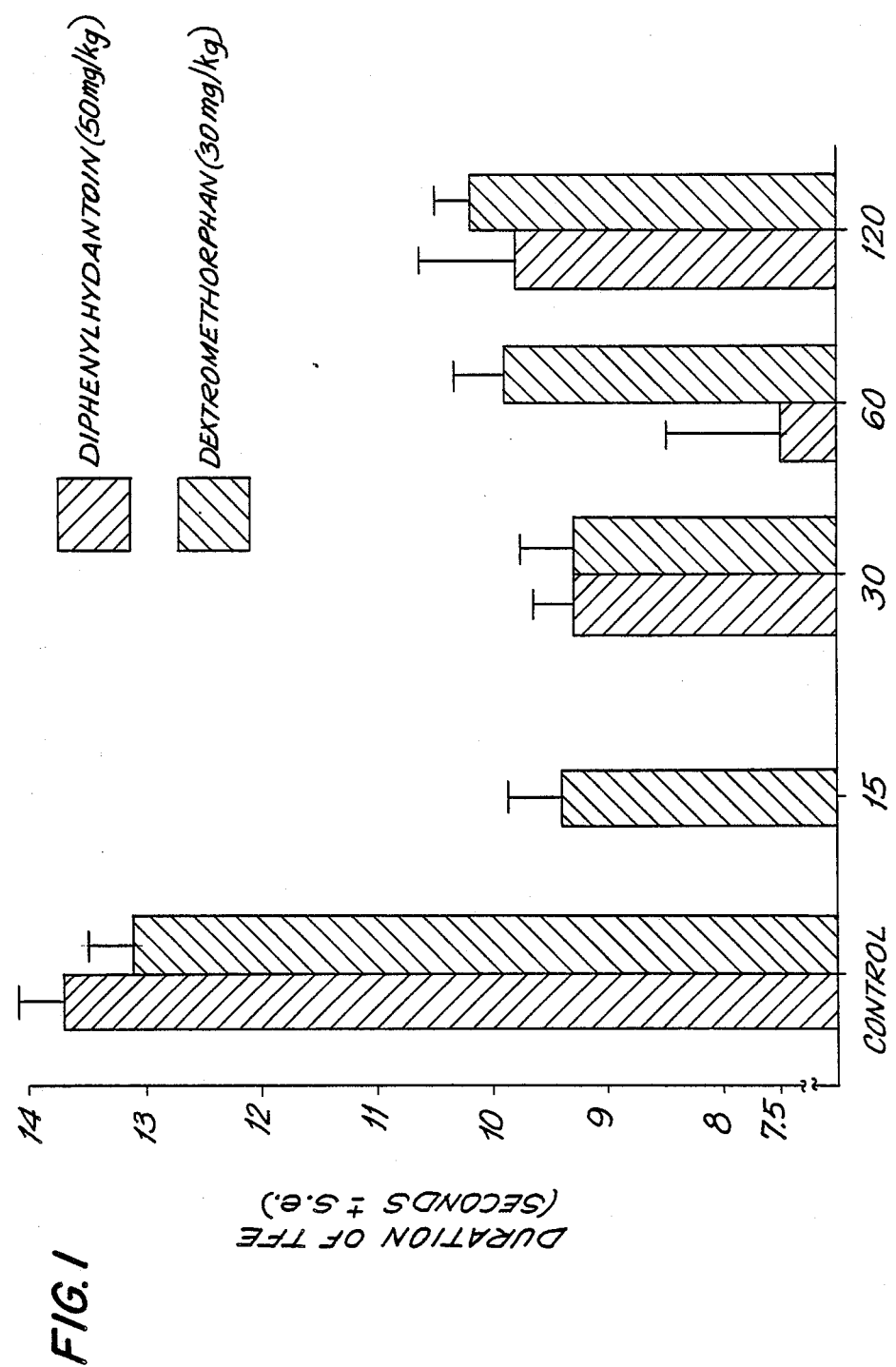
FIG. 1 is a bar diagram showing the duration of tonic forelimb extension as a function of the amount of anticonvulsant agent administered.

One aspect of the present invention is directed to an anticonvulsant composition comprising as an active ingredient an amount of a compound selected from the group consisting of dextromethorphan and non-narcotic, nonaddictive, low-toxicity compounds that bind to the same central nervous system sites as dextromethorphan with at least about the same affinity for said sites, said amount being effective for controlling seizures in mammals.

Another aspect of the present invention is directed to an anticonvulsant composition comprising as active ingredients (a) an antiepileptic hydantoin or noscapine, and (b) a compound selected from the group consisting of dextromethorphan and other non-narcotic, nonaddictive, low-toxicity compounds that bind to the same central nervous system sites as dextromethorphan with at least about the same affinity for said sites; wherein the amount of the active ingredients in combination is effective for controlling seizures in mammals, and the amount of said compound is at least sufficient to potentiate said hydantoin or noscapine.

Still other aspects of the present invention are directed to dosage forms comprising amounts of the aforementioned compositions effective for controlling seizures in mammals.

Yet another aspect of the present invention relates to a method for controlling seizures in a mammal in need of such treatment comprising administering to said mammal an amount effective for controlling seizures of a compound selected from the group consisting of dextromethorphan and non-narcotic, nonaddictive, low-toxicity compounds that bind to the same sites in the central nervous system as dextromethorphan with at least about the same affinity for said sites as dextromethorphan.

Another aspect of the present invention relates to a method for controlling seizures in a mammal in need of such treatment comprising administering to said mammal an amount of an antiepileptic hydantoin (or noscapine) and an amount of dextromethorphan or another non-narcotic, nonaddictive, low-toxicity compound that binds to the same central nervous system sites as dextromethorphan with at least about the same affinity, said amounts in combination being effective for controlling seizures in said mammals, said amount of DM or said other compound being at least sufficient to potentiate DPH.

DETAILED DESCRIPTION OF THE INVENTION

The present inventors have discovered that the non-opiate antitussive DM and several other compounds that bind to the same central nervous system (CNS) site as DM with at least about the same affinity are effective anticonvulsant agents and also potentiate the anticonvulsant action of DPH and other antiepileptic hydantions, thus substantially lowering the minimun mum effective dose of DPH, and other hydantoins. As a result, the amount of hydantoin necessary for antiepileptic activity in a given case is substantially lower than that which would have been effective for the same purpose, if the hydantoin had been used alone.

Any one of a number of nonaddictive, non-narcotic compounds of low toxicity that effectively compete with DM for the same central nervous system binding sites could be used to potentiate DPH. Such compounds include but are not limited to non-opiate antitussives that bind to the same CNS sites as DM. Specific examples of compounds that can be used in the compositions of the present invention include benztropine, chlorpromazine, perphenazine, fluphenazine, trifluoperazine, prochlorperazine, alpha-flupenthixol, trimeprazine, dimethoxanate, opipramol, promethazine, pipazethate, carbetapentane, caramiphen, and noscapine as well as pharmaceutically acceptable derivatives, homologs, isomers, analogs and organic and inorganic addition salts thereof having therapeutic activity as provided herein. For example, the DM analogs that have the groups -CH₂(CO)CH₃ and CH₂CH(CH₃)OH instead of CH₃ as N-position substituents can be used. The methylsulfonate salt of benztropine, the hydrochloride and ethanedisulfonate salts of caramiphen, the citrate salt of carbetapentane, the maleate and hydrochloride salts of chlorpromazine, the dihydrochloride salt of flupenthixol and fluphenazines are some examples of the forms of the above compounds that can be used in the compositions of the present invention.

Preferred are perphenazine, fluphenazine, trifluoperazine, opipramol, and carbetapentane with DM being most preferred. These compounds have anticonvulsant activity independent of their DPH-potentiating action.

The structural formulas and IUPAC names of these compounds are given in Table I below.

TABLE I benztropine: 3-(diphenylmethoxy)-8-methyl-8-azabicyclo[3.2.1]octane

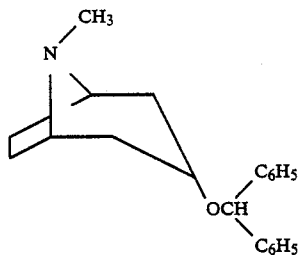

caramiphen: 1-phenylcyclopentanecarboxylic acid 2-(diethylamino)ethyl ester

carbetapentane: 1-phenylcyclopentanecarboxylic acid 2-(2-diethylaminoethoxy)ethyl ester

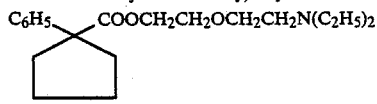

chlorpromazine: 2-chloro-N,N-dimethyl-10H-phenothiazine-10-propanamine

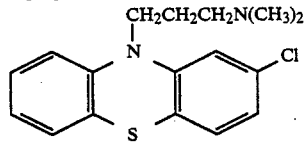

dimethoxanate: 10H-phenothiazine-10-carboxylic acid 2-[2-(dimethylamino)ethoxy]ethyl ester

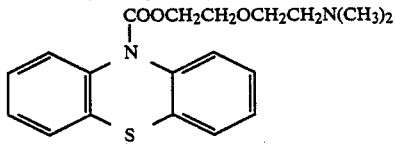

flupenthixol: 4-[3-[2(trifluoromethyl)-9H-thioxanthen-9-ylidene]propyl]-1-piperazineethanol TABLE I-continued

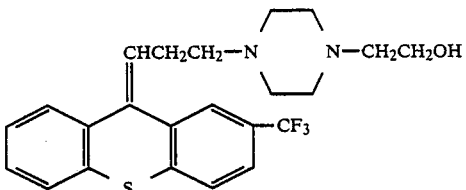

fluphenazine: 4-[3-[2-(trifluoromethyl)-10H-phenothiazin-10-yl]propyl]-1-piperazineethanol

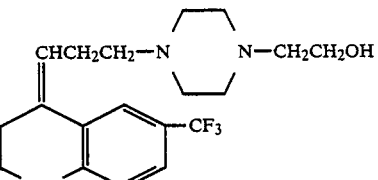

opipramol: 4-[3[(5H-dibenz[b,f]azepin-5-yl)propyl]-1-piperazineethanol

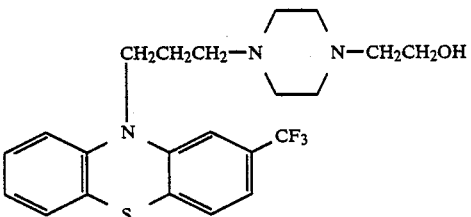

perphenazine: 4-[3-(2-chlorophenothiazin-10-yl)propyl]-1-piperazineethanol

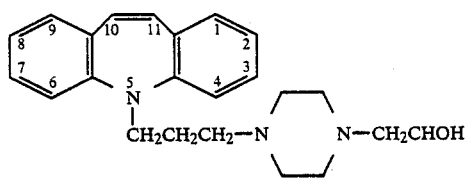

pipazethate: 10H-pyrido[3,2-b][1,4]benzothiadiazine-10-carboxylic acid 2-(2-piperidinoethoxy)ethyl ester

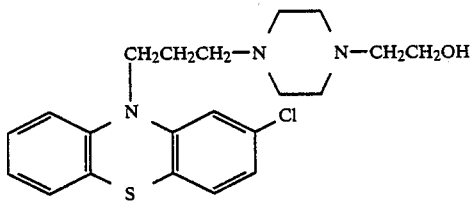

prochlorperazine: 2-chloro-10-[3-(4-methyl-1-piperazinyl)propyl]-10H-phenothiazine

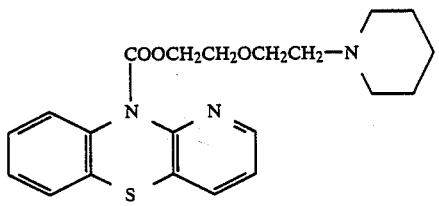

promethazine: N,N,alpha-trimethyl-10H-phenothiazine-10-ethanamine

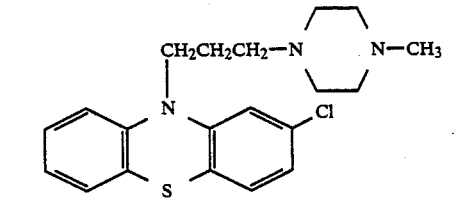

TABLE I-continued

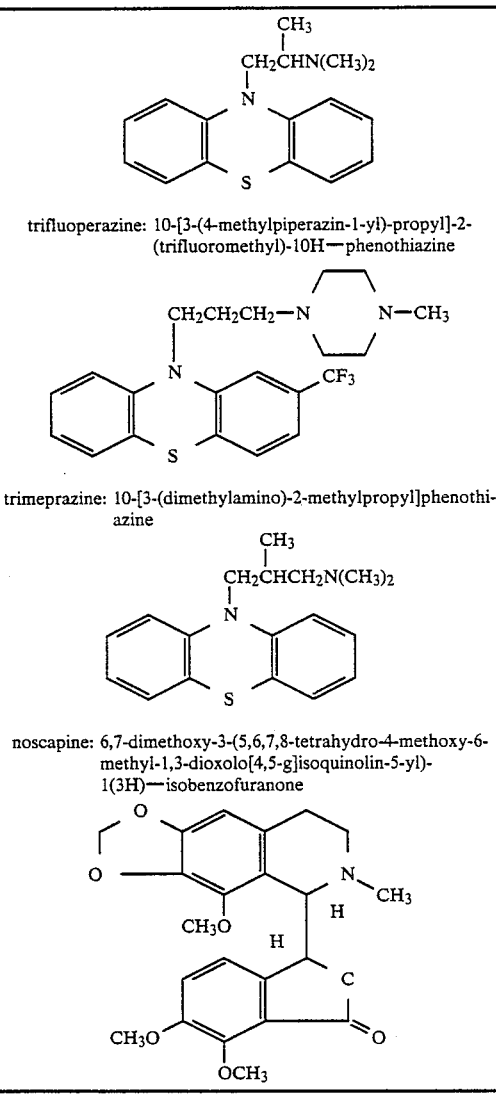

trifluoperazine: 10-[3-(4-methylpiperazin-1-yl)-propyl]-2-(trifluoromethyl)-10H—phenothiazine trimeprazine: 10-[3-(dimethylamino)-2-methylpropyl]phenothiazine noscapine: 6,7-dimethoxy-3-(5,6,7,8-tetrahydro-4-methoxy-6-methyl-1,3-dioxolo[4,5-g]isoquinolin-5-yl)-1(3H)—isobenzofuranone The above compounds can be obtained from commercial sources such as:
DPH: Polychemicals Laboratories, Bronx, N.Y.
DM: Hoffman-La Roche, Nutley, N.J. benztropine: Merck Sharp and Dohme West Point, Pa.
carbetapentane: CM/K&K Life sciences Group, Cleveland, Ohio
flupenthixol: Smith Kline French, Philadelphia, Pa.
opipramol: Ciba-Geigy, Summit, N.J.
mephenytoin: Sandoz Pharmaceuticals, Inc., East Hanover, N.J.
ethotoin: Abbott Laboratories, North Chicago, Ill.
noscapine: Mallincrodt Pharmaceutics, St. Louis, Mo.
or can be synthesized using well-known techniques, such as described in U.S. Pat. Nos. 2,409,754; 2,595,405; Swiss Pat. No. 234,452; British Pat. No. 753,799; U.S. Pat. Nos. 2,404,588; 2,645,640; 2,778,824; British Pat. No. 925,538; U.S. Pat. No. 3,194,733; Swiss Pat. Nos. 359,143 and 360,061; U.S. Pat. Nos. 2,860,138; 2,989,529; 2,902,484; 2,530,451 and 2,607,773; 2,921,069; 2,837,518; 2,676,177; and 3,108,106, the disclosure of which is incorporated by reference herein. In addition to DPH, other antiepileptic hydantoins can be advantageously potentiated by DM and compounds that bind to the same brain sites. These include mephenytoin, N-demethylated mephenytoin, and ethotoin. However, DPH is preferred.

The compositions of the present invention can be administered orally or parenterally (subcutaneously or intravenously because intramuscular injection is not indicated for DPH-containing compositions).

In the case of potentiated DPH compositions, it is not essential that DPH and the potentiating compound be administered simultaneously or in the same dosage form. Sequential administration is acceptable. However, simultaneous administration is preferred.

The active ingredients in the oral dose are preferably administered in the form of a tablet, pill, capsule or other solid dosage unit. Coating of the tablet or protective capsule is desirable to facilitate swallowing or to prevent unpleasant taste. Suitable coatings may be prepared from aqueous suspension containing sugar and insoluble powders such as starch, calcium carbonate, talc or titanium dioxide suspended with a suitable mixing agent such as gelatin. Film coatings consisting of water-soluble or dispersible materials such as hydroxypropylmethylcellulose, cellulose, methylcellulose, carboxymethycellulose, and mixtures of cellulose acetate phthalate and polyethylene glycol applied out of aqueous or nonaqueous solvents are suitable for coating the tablets and pills made according to the present invention. Soft shell gelatin capsules of the type normally used as pharmaceutical coatings are also suitable as dosage forms for the invention. Of course, the capsules may comprise any well-known pharmaceutically acceptable material such as gelatin, cellulose derivatives or the like.

The active ingredients of the present invention may be compounded in the desired oral form in combination with inert ingredients including fillers such as talc, lactose, starch, bentonite, diatomaceous earth, lubricants and food flavorings. Tablets for use in the present invention may be made by punching or compressing the active ingredients and the fillers in a tabletting machine.

Liquid oral doses in the form of solutions and suspensions are also suitable for use in the present invention as are suppositories for rectal administration. In making solutions and suspensions, the active ingredients may be dissolved or suspended in distilled water containing a small amount of alcohol to facilitate hydantoin suspension, conventional U.S.P. syrup formulations and any other pharmaceutically acceptable carrier liquid.

For parenteral administration the compounds of the invention are dissolved in a pharmaceutically acceptable injectable carrier liquid. A preferred carrier liquid for DPH includes polypropylene glycol and alcohol in water (pH:12 by addition of NaOH) and would be a suitable carrier for the potentiated compositions of the present invention.

When used as anticonvulsants in mammals, the compositions of the present invention containing DM (or one or more of the compounds that bind to the same site) can generally be administered at a dosage level from about 15 to about 200 milligrams and preferably from about 30 to about 150 milligrams of active ingredient two or three times a day.

The potentiated compositions containing DPH can generally be administered at a dosage level of DPH ranging from about 50 to about 500 mg per day for adults (preferably about 100 to 300 mg) and from about 1 to about 8 mg of DPH per kg body weight/day for children.

In these potentiated DPH-containing compositions, the amount of DPH necessary for effectiveness is usually substantially lower than it would have been if DPH had been used alone to control the epilepsy. The amount of the potentiating compound should be at least sufficient to potentiate the DPH i.e. at least sufficient to lower the minimum effective dose of DPH. The noscapine doses are comparable to the ones given for DPH.

Although subthreshold levels of the potentiating compound have sufficient Potentiating activity when used in conjunction with DPH, the potentiated compositions of the present invention are not limited to containing subthreshold levels of the potentiating compound.

The daily effective dosage, or the dosage required to prevent or inhibit or control convulsions from a particular disease or stimulant depends on the condition being treated, the individual characteristics of each mammal being treated and the nature of the physical or chemical stimulus inducing or responsible for the convulsive activity. Thus, the exact dose required to alleviate convulsions attributable to a particular disorder or stimulus or their effects will vary within the range discussed above from one patient to another and is subject to optimization, which can be carried out by conventional and convenient experimental techniques.

Solid pharmaceutical dosage forms such as pills, capsules, or tablets may contain from about 40 to 300 milligrams of active ingredient, or combination of active ingredients. More specifically, such dosage forms may contain from about 15 to 200 mg of DM (or other potentiating compound) and from about 25 to 100 mg of DPH (or other hydantoin).

The liquid oral dosage forms of the present invention are preferably administered in the form of a solution or suspension in a pharmaceutically acceptable vehicle. Liquid dosages containing from about 9 to about 60 milligrams of active ingredient (or combination of active ingredients) per cubic centimeter of vehicle are useful in administering these agents to mammals.

The liquid Parenteral dosage forms of the present invention may contain from about 9 to about 60 mg of active ingredient or combination of active ingredients per ml of vehicle.

Suppository dosage forms may be prepared by incorporating an active agent into a base material that can be formed into the desired shape. Suitable base materials include cocoa butter, glycerinated gelatin, hydrogenated begetable fats, mixtures of polythethylene glycols of various molecular weights and fatty acid esters of polyethylene glycol. Suppositories for adults may contain from about 40 to about 300 milligrams of active ingredient or combination of active ingredients.

The invention is further described below by reference to specific examples, which are intended to illustrate the invention without limiting its scope.

EXAMPLES:

The anticonvulsant activity of the instant compositions was measured by inducing maximal electroshock seizures (MES) in rats using the following standard testing conditions:

Animals. Male, Sprague Dawley rats (200–300 g from Zivic Miller, Alison Park, Pa.) were used for all experiments. Upon delivery, the animals were housed individually in a temperature controlled room with a standard 12-hour light-dark cycle (lights on 600 hr to 1800 hr). Food and water were available ad libitum.

Figure 2:
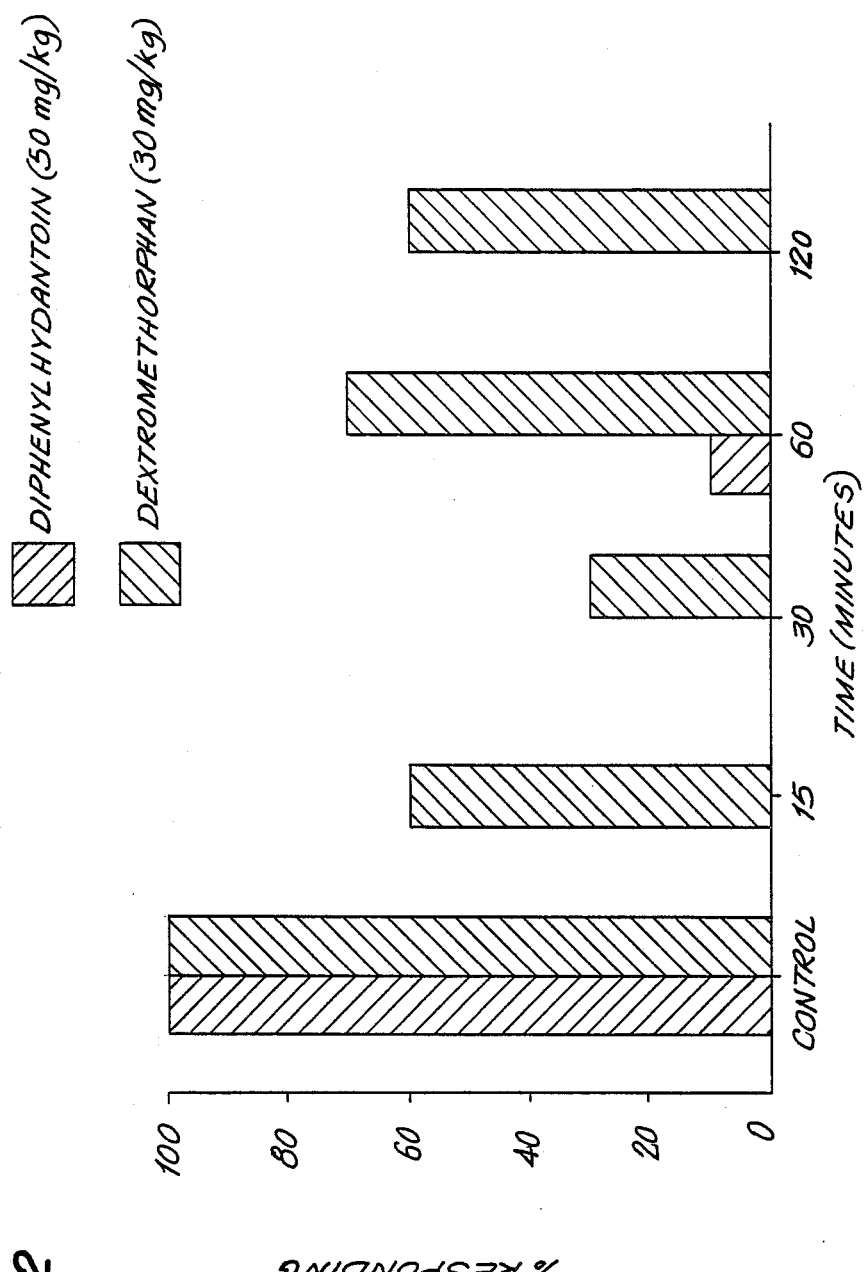
FIG. 2 is a bar diagram showing the presence of seizure activity, as a function of the amount of anticonvulsant administered.
Figure 3:
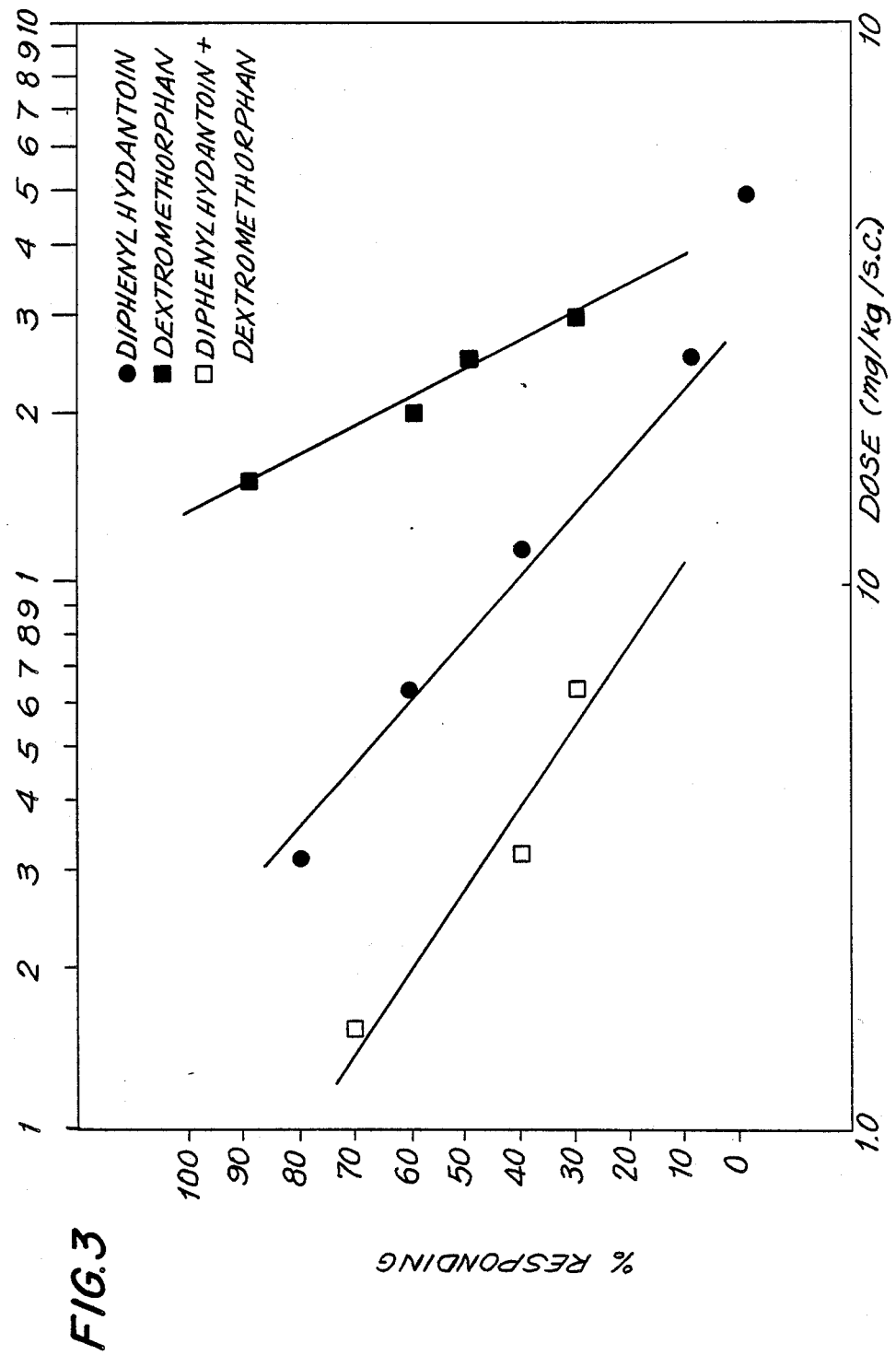
FIG. 3 is a semilog plot of the doses at which a given anticonvulsant composition controls seizure activity of a percentage of the subjects tested.
Figure 4:
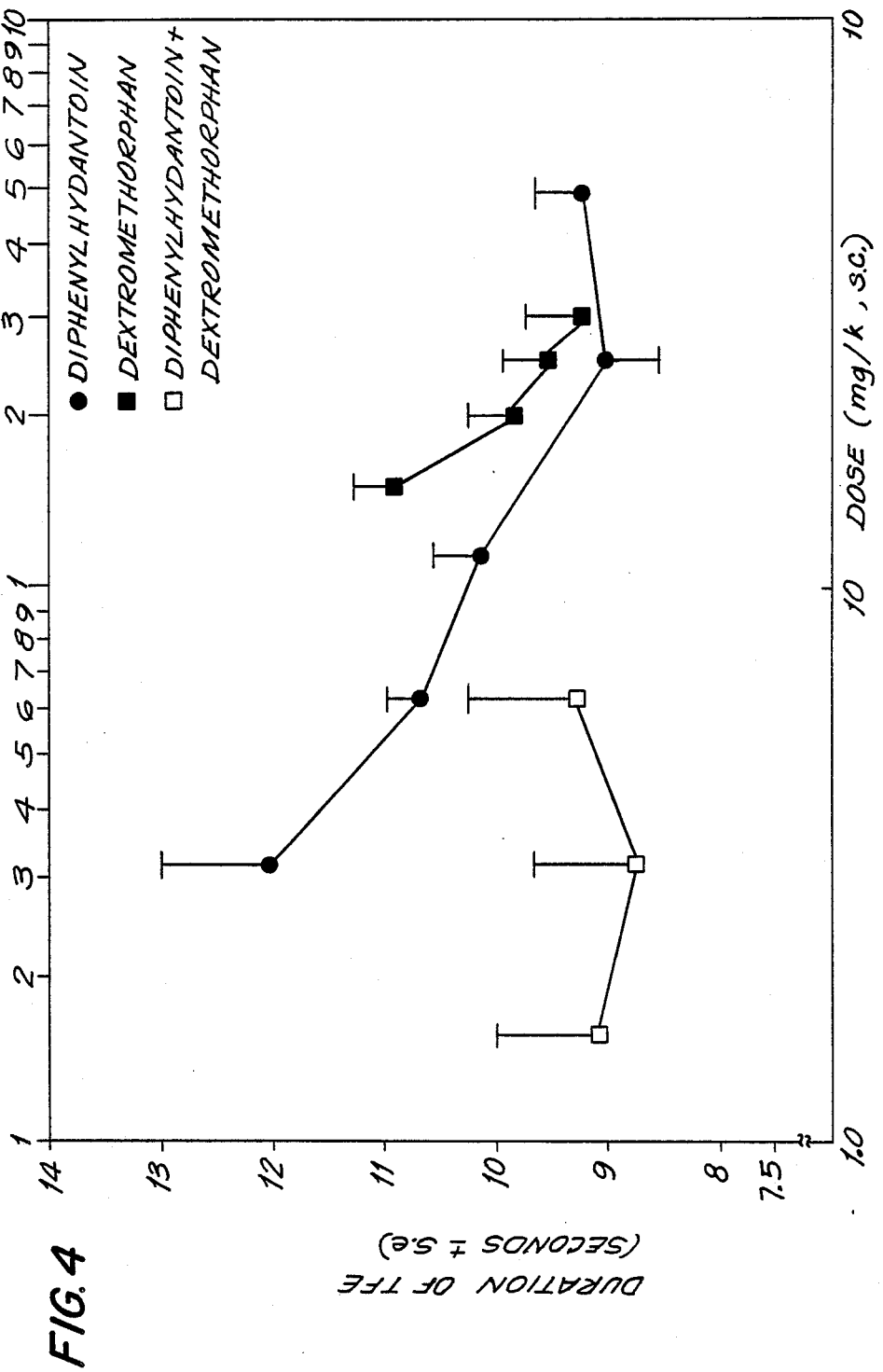
FIG. 4 is a semilog plot of the doses at which a given anticonvulsant composition limits the duration of tonic forelimb extension.

Maximal electroshock seizures (MES). Supramaximal (tonic extension of the hindlimbs) seizures were induced electrically by means of a Wahlquist shock apparatus (Wahlquist Inst., Salt Lake City, Utah) with a built-in high internal resistance designed to provide a constant current across animals. A 60-Hz, 50 mA current was delivered transauricularly for 2.0 seconds via small alligator clips attached to the pinna of each ear. This current intensity elicited complete tonic anticonvulsant effect occurred with 15–30 minutes following DM administration and within 30–60 minutes following the injection of DPH, with significant anticonvulsant action still evident two hours later (FIGS. 1 and 2). The anticonvulsant $ED_{50}$ (95% CL) for the effect of DM to block THE was 24.1 mg/kg (19.7–29.5) (FIG. 3). The tests show DM to be only 3 times less potent than DPH as an anticonvulsant in the rat. In addition, the simultaneous administration of a subthreshold dose of DM (15 mg/kg) increased the potency of DPH (FIGS. 3 and 4), lowering the anticonvulsant $ED_{50}$ for DPH threefold to 2.79 mg/kg (14.4–5.43) in the MES test (FIG. 3). In fact, additional preliminary tests indicate that DM is able to increase the potency of DPH more than threefold.

At the time of testing, the DM- and DM/DPH-treated animals exhibited normal exploratory behavior when placed in the novel testing environment. There were no signs of overt sedation, ataxia or motor impairment at any time after drug administration.

The above results indicate that the co-administration of DM and DPH has a synergistic effect in that the former (even at subthreshold levels) potentiates the latter. A three-fold decrease of the $ED_{50}$ of DPH would significantly lower the incidence and severity of its side effects.

Examples

The anticonvulsant activity of carbetapentance by inducing maximal electroshock seizures (MES) in rats following the standard testing conditions previously described.

Experimental Protocol

Drug treated groups received a single subcutaneous injection of DPH (0.28 to 25.0 mg/kg), and/or carbetapentance C b P (6.25 to 50 mg/kg) or noscapine (20 to 60 mg/kg), a non-opioid antitussive. control groups received the appropriate vehicle injections as follows: carbetapentane citrate (Wallace Laboratories) and diphenylhydantoin (Warner-Lambert) were dissolved in distilled, deionized water. To solubilize, the DPH suspension was adjusted to pH 12 with sodium hydroxide. All the drug solutions were prepared immediately prior to testing, and for each test group the appropriate vehicle controls were used.

All injections were given as a 1 ml/kg volume. All the animals tested were naive to drug and seizure exposure, and each animal was used only once. For the time-course studies, each animal was subjected to an M E S seizure at times ranging from 15 to 120 minutes following injections. The dose-response experiments were done at 30 minutes postinjection, the time of peak drug response.

The anticonvulsant drug DPH caused a dose-related protection against MES seizures, decreasing the incidence of THE from 100 to 0% (FIG. 3) and the duration of TFE a maximum of 34% (FIG. 4) from 13.7=0.4 to 9.1=0.5 seconds. The anticonvulsant $ED_{50}$ for DPH-induced blockade of T H E was $3.0 \times 10^{-5}$ mol/kg.

Figure 5:
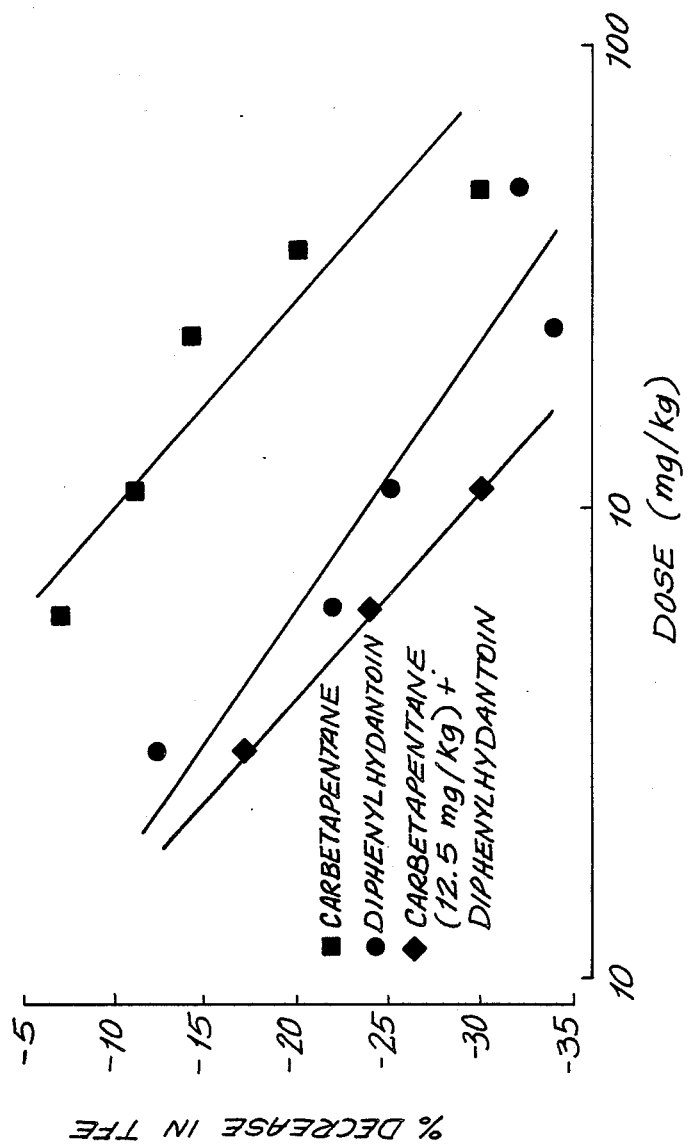
FIG. 5 is a semilog plot of the percent decrease in tonic forelimb extension as a function of the dose of given anticonvulsant compositions.
Figure 6:
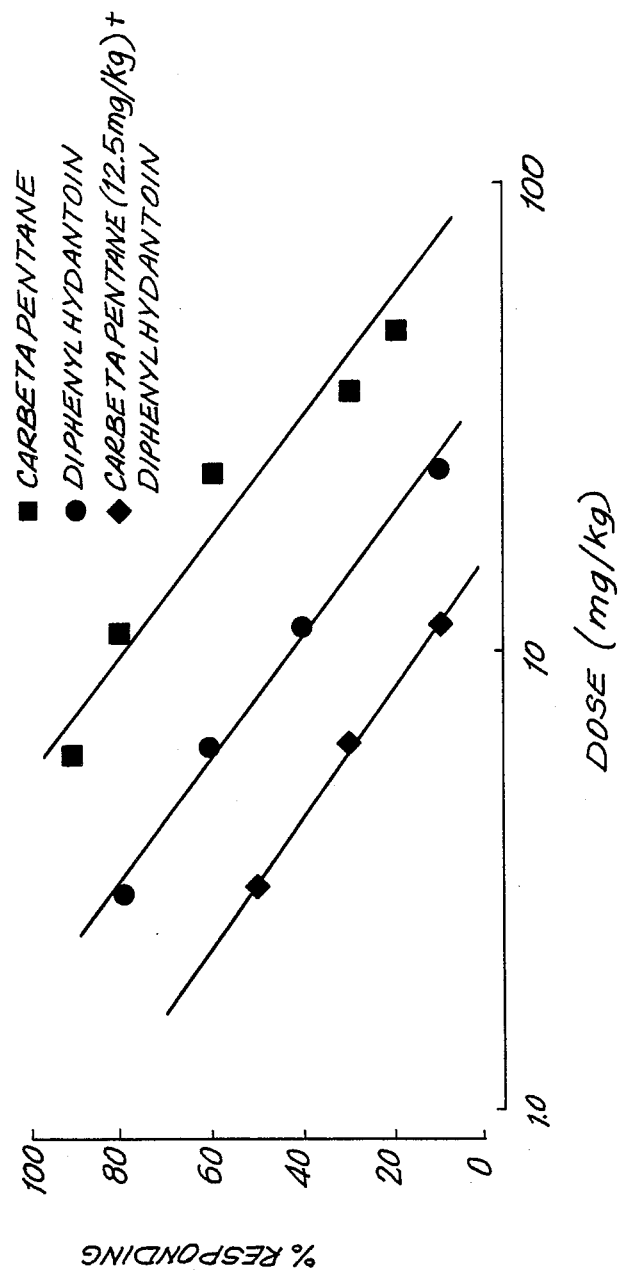
FIG. 6 is a semilong plot of the precent of the subjects tested which responded to given anticonvulsant compositions as a function of dose.

We initiated studies on the effects of an additional non-opioid antitussive agent: carbetapentane (CPB), which displays high affinity for the DM site. We have found that CBP is also an effective anticonvulsant in this test (FIGS. 5 and 6), with a duration of action similar to DM (data not shown) and a potency intermediate between that of DPH and DM (Table 2). Moreover, like DM, the simultaneous administration of a subthreshold dose of CBP (12.5 mg/kg) caused a parallel shift to the left in the dose-response curve for DPH (FIG. 6) and lowered its $ED_{50}$ nearly threefold to $1.2 \times 10^{-5}$ mol/kg (Table 2), thereby potentiating the anticonvulsant action of DPH.

Furthermore, the simultaneous administration of DM or CBP with DPH did not alter the overt behavior of DPH-treated animals.

TABLE II

Figure 7:
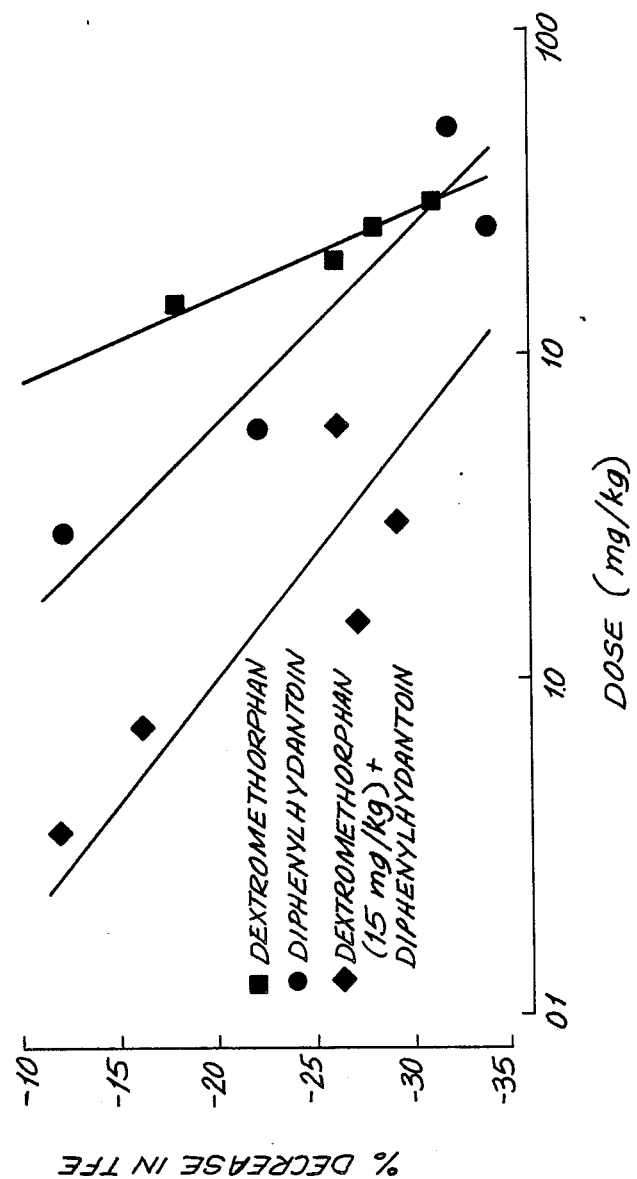
FIG. 7 is the same type of plot as FIG. 5 for a different set of anticonvulsant compositions.

Anticonvulsant potencies calculated from the dose-response data shown in FIG. 2. The $ED_{50}$ values and 95% confidence limits (CL) were calculated using the method of Litchfield and Wilcoxin (supra). The $A_{50}$ values represent the dose required to produce a 50% decrease in the duration of TFE. These values were estimated from the regression lines plotted in FIGS. 7a and 5c. FIG. 7 was generated from the data of FIG. 3. All values are expressed as mol/kg $\times 10^{-5}$. Therefore, potency comparisons between the various treatments were made on the basis of molecular weight. *As noted in the text and in FIGS. 5 and 6, these DPH-treated groups were pretreated with subthreshold doses of CBP and DM, respectively.

| Treatment | $ED_{50}$ (CL) | $A_{50}$ |
|---|---|---|
| DPH | 3.0 (1.8–4.9) | 1.6 |
| CBP | 4.8 (3.1–7.2) | 3.3 |
| DM | 6.2 (5.1–7.6) | 3.2 |
| CBP + DPH* | 1.2 (0.6–2.3) | 0.8 |
| DM + DPH* | 1.0 (0.5–2.0) | 0.2 |

EXAMPLE 3

The anticonvulsant activity of caramiphen by induction of MES was demonstrated in rats following the standard testing conditions previously described.

On the day of the experiment animals were randomly assigned to control or drug-treated groups (n=10 per group). Both groups were subjected to a single transauricular MES delivered through miniature alligator clips attached to the pinna of each ear. The alternating current stimulus was delivered using a Wahlquist shock apparatus (Wahlquist Inst. Co., Salt Lake City) with built-in high internal resistance so as to provide constant current across animals. The stimulus parameters were 2.0 sec at 60 Hz, 5 mA. Critical to the discriminatory nature of the seizure model and defining the anticonvulsant profile of a test compound (Swinyard and Woodbury, Antiepileptic Drugs 2nd Ed., p. 111 (Raven Press) 1982; Piredda et al., J. Pharmacol. Exp. Ther., 232, 741, 1985), these stimulus parameters have been pharmacologically defined as supramaximal (Tortella et al., Brain Res., 383, 314 1986). In general, MES causes a generalized "spreading" convulsion characterized by an initial tonic extension of the forelimbs (TFE), progressing immediately to tonic hindlimb extension (THE) followed by clonic jerking. In the present study, each convulsion was scored for the presence or absence of THE, and the duration of the convulsion was recorded as the duration of TFE.

Figure 8:
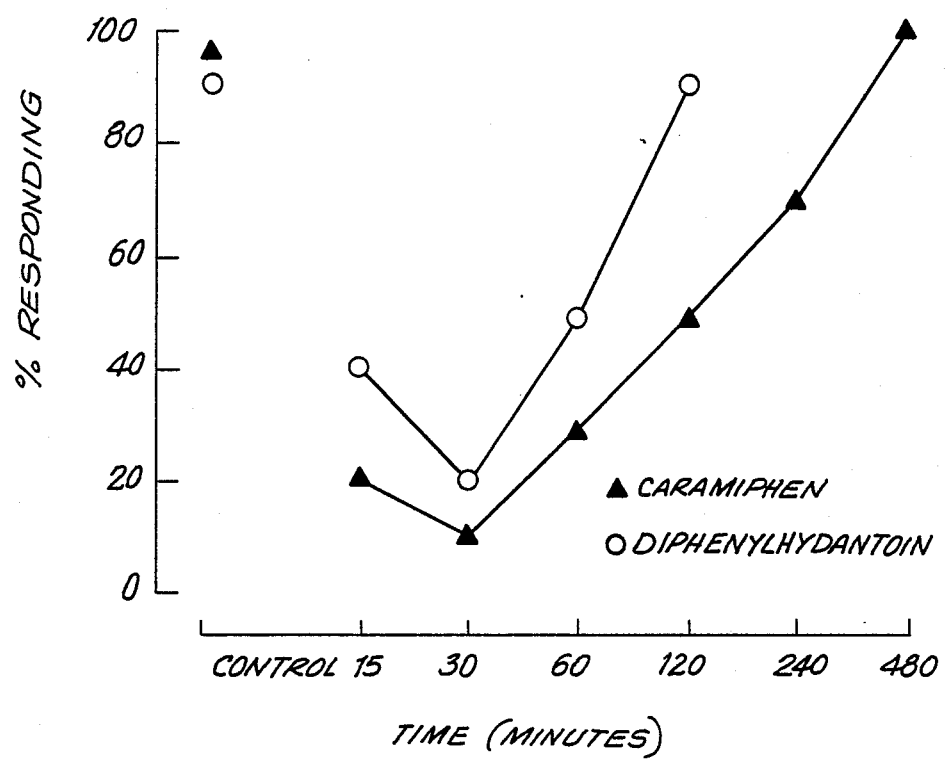
FIG. 8 is a plot of the number of subjects tested which responded to given anticonvulsant compositions as a function of time.

Drug-treated groups were administered a single subcutaneous (s.c.) injection of diphenylhydantoin (0.28–25.0 mg/kg) or caramiphen (6.25–50.0 mg/kg). In all cases control groups received the respective vehicle treatments (1 ml/kg, s.c.). At the time of testing all the animals were naive to drug and seizure exposure, and each animal was used only once throughout the study. For the dose-response studies testing occurred 30 min post-injection, the time of peak drug response as determined from time-course experiments. The results are shown in FIG. 8 which is a plot of the percent response against time from the administration of the drug. The time-course experiments were conducted using doses of the respective drugs producing equivalent responses at 30 min post-injection.

For the interaction experiments, a subthresholdeffective dose of caramiphen (6.25 mg/kg, s.c.) was given immediately prior to diphenylhydantoin (0.065–12.5 mg/kg s.c.). The animals were then subjected 30 min later to MES as described above.

Since caramiphen has weak atropine-like properties (Kraatz et al., J. Pharmacol. Exp. Ther. 96, 42, 1949; Herz et al., Int. J. Neuropharmacol., 4, 207, 1965), separate experiments were aimed at determining whether the effects of caramiphen in the MES test reflected cholinolytic properties of the drug. In one experiment, animals were pretreated with physostigmine (0.1 mg/kg, s.c.) 30 min prior to caramiphen (12.5–50.0 mg/kg, s.c.) and tested 30 min later as described above. In a second experiment, atropine sulfate (25.0–300 mg/kg, s.c.) was administered to groups of naive rats (n=10) 30 min prior to MES.

The behavioral effects of caramiphen and diphenylhydantoin were evaluated using subjective and objective measures of overt behavior. In addition to the positional sense test and the gait and stance test routinely used to evaluate behavioral effects of anticonvulsant compounds (Porter et al., Cleveland Elin. Q., 51, 293, 1984), the behavioral effects of caramiphen and diphenylhydantoin were also determined in a multiple schedule paradigm of non-punished responding (FR 30) for food (Witkin et al., Psychopharmacol, 84, 16, 1984).

Caramiphen (Smith-Kline and French), diphenylhydantoin (Warner-Lamert), atropine sulfate (Aldrich) and physostigmine (Aldrich) were dissolved in distilled deionized water. Diphenylhydantoin was solubilized by adjusting the pH to 12 with sodium hydroxide. All the compounds were prepared daily immediately prior to testing and administered according to body weight.

The $ED_{50}$ values and 95% confidence limits (CL) were calculated using the method of Litchfield and Wilcoxon, J. Pharmacol. Exp. Ther., 96, 99, (1949). Regression lines were analyzed for linearity (r=correlation coefficient). For direct comparisons, the Student's t-test was used. All the statistical procedures were performed using the computer programs described by Tallarida and Murray, Manual of Pharmacologic Calculation, (1981).

ANTICONVULSANT EFFECTS OF CARAMIPHEN

Figure 9:
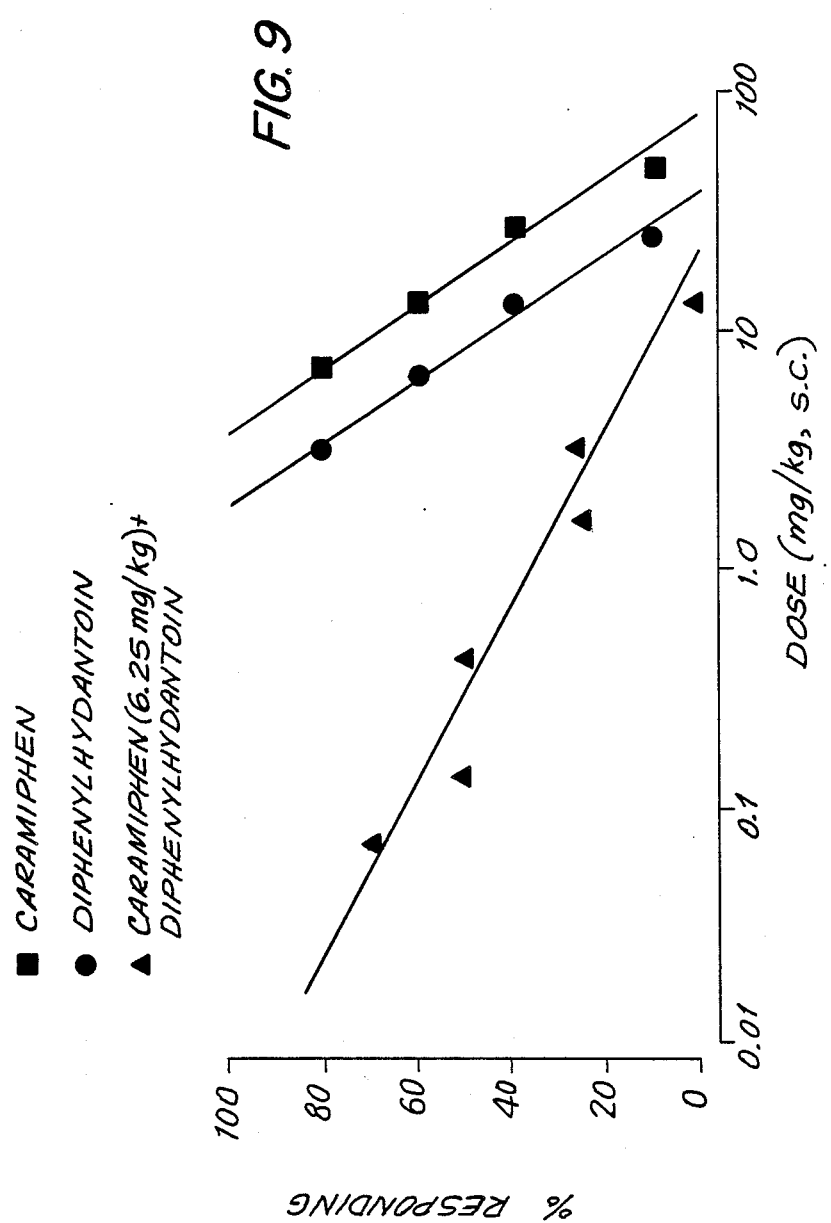
FIGS. 9 and 10 are the same type of plot as FIG. 6 for different given sets of anticonvulsant compositions.

Maximal electroshock resulted in THE in 90–100% of the control animals tested. The time-course data for the anticonvulsant actions of caramiphen are shown in FIG. 8. Peak protection was observed within 30 min, with an anticonvulsant duration of action persisting for at least 4 h. The anticonvulsant effects of caramiphen were dose-dependent and linear (r=0.99) (FIG. 9). The anticonvulsant ED$_{50}$ was 29 umol/kg or 14 mg/kg (Table III).

Behaviorally, caramiphen failed to produce any apparent signs of neurological deficit in gait, posture or tremor. There was no evidence of behavioral sedation, lack of exploratory behavior, or respiratory depression noted upon evaluation of overt behavior. As shown in Table IV, the anticonvulsant ED$_{50}$ of caramiphen (14 mg/kg) had no significant depressant effect on non-punished responding. However, at 2×ED$_{50}$ (28 mg/kg) significant decreases in level-pressing were seen.

The protective effects of the anticonvulsant standard diphenylhydantoin were also dose- and time-dependent. Maximal protective effects occurred with 30 min post-injection with a duration of action of 1-2 h (FIG. 8). The dose-relationship for diphenylhydantoin was linear (r=0.99), with an ED$_{50}$ value of 30 umol/kg (Table III). Diphenylhydantoin had no overt behavioral depressant effects, nor were significant depressant effects measured on non-punished responding (Table IV).

Comparisons of the relative potency and duration of action for caramiphen and diphenylhydantoin indicated that on a molecular weight basis caramiphen was slightly more potent than diphenylhydantoin as an anticonvulsant (Table III), and longeracting (FIG. 8). The effect of a subthreshold-effective dose of caramiphen (6.25 mg/kg) on the anticonvulsant properties of diphenylhydantoin (0.063-12.5 mg/kg) is shown in FIG. 9. Pretreatment with caramiphen caused a leftward shift in the diphenylhydantoin dose-response curve (r=0.96), increasing the relative potency of diphenylhydantoin 33-fold (ED$_{50}$=0.9 umol/kg) (Table III).

Figure 10:
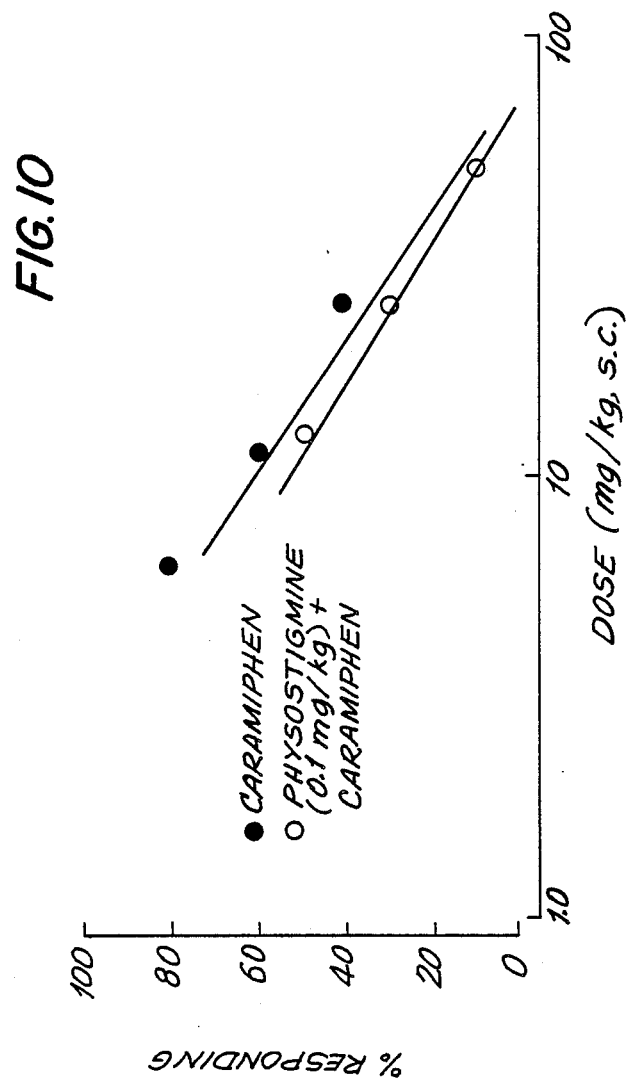

Physostigmine (0.1 mg/kg) failed to antagonize the protective effects of caramiphen (FIG. 10). It should be noted that despite its own rate-decreasing activity (Table IV), this dose of physostigmine was an antagonist of the depressant effects of caramiphen (28 mg/kg) and atrophine (30 mg/kg) on non-punished responding (Table IV).

Atrophine, even at doses as high as 300 mg/kg, was only marginally protective against MES-induced seizures. The effect of atrophine on THE was not dose-related and the duration of TFE remained unchanged compared to controls (Table V).

The present results indicate that caramiphen is a potent anticonvulsant in this test and enhanced the protective effects of diphenylhydantoin. The anticonvulsant profile of caramiphen demonstrates that it is more potent than any of the compounds tested to date, including diphenylhydantoin, and that it possesses a far greater ability than dextromethorphan or carbetapentane to enhance the potency of diphenylhydantoin (See Table III). Furthermore, the behavioral effects of caramiphen appear minimal, with no signs of behavioral depressions being manifested until 2×ED$_{50}$ dose.

The anticonvulsant effects of caramiphen were dose-related, linear and time-dependent. Caramiphen was nearly twice as potent as diphenylhydantoin and is 3-4 times more potent than either dextromethorphan or carbetapentane (Table III).

In the experiments described here the anticonvulsant effects of caramiphen were not antagonized by a pharmacologically effective dose of physostigmine. Furthermore, atropine itself was found to be weakly effective against MES convulsions even when tested at doses 25 times greater than the minimally effective dose of caramiphen. Since, with the exception of benztropine, muscarinic agents such as atropine, scopolamine, trihexiphenidyl, and oxotremorine are not potent competitors of [$^3$H]dextromethorphan binding (Craviso and Musacchio, Mol. Pharmacol. 23, 619, 1983), it seems unlikely that cholinolytic activity contributes significantly to the anticonvulsant effects of caramiphen demonstrated in this study.

Despite ambiguities regarding the mechanism of action of diphenylhydantoin, and the role of dextromethorphan receptors in the anticonvulsant pharmacology of the non-opioid antitussives, the allosteric interaction of dextromethorphan and diphenylhydantoin in binding assays (Craviso and Musacchio, Mol. Pharmacol., 23, 629, 1983a), and the in vivo potentiation of diphenylhydantoin by dextromethrophan and carbetapentane (Tortella and Musacchio, Brain Res., 383, 314, 1986) or caramiphen demonstrated above indicate that these compounds may interact by allosteric coupling of different binding sites. The functional consequence of this allosteric interaction is a lowering of the anticonvulsant ED$_{50}$ for diphenylhydantoin (demonstrated in Table III). The importance of this interaction resides with the potential of non-opioid antitussives like caramiphen to dramatically reduce the daily maintenance dose of prototypic anticonvulsants such as diphenylhydantoin which, while highly efficacious, suffer from chronic toxicity not associated with their specific pharmacological actions (Rall and Schleifer, MacMillan, New York, p. 446, 1985). All cited literature is incorporated by reference.

TABLE III

Summary of the anticonvulsant potency of the non-opioid antitussives and their enhancement of diphenylhydantoin effectiveness.

| Treatment | ED$_{50}$ (95% CL) umol/kg | Potency Ratio |
|---|---|---|
| Diphenylhydantoin | 39 (18–49) | 1.0 |
| Caramiphen | 18 (10–33) | 1.7 |
| Carbetapentane | 48 (31–72) | 0.6 |
| Dextromethorphan | 62 (51–76) | 0.5 |
| Caramiphen[2] + Diphenylhydantoin | 0.9 (0.07–10) | 33.3 |
| Carbetapentane[2] + Dephenylhydantoin | 12 (6.0–23) | 2.5 |
| Dextromethorphan[2] + Dephenylhydantoin | 10 (5.0–20) | 3.0 |

[2]The doses of caramiphen; carbetaphentane and dextromethorphan were 6.25, 12.5 and 15 mg/kg, respectively.

TABLE IV

The effect of the various test compounds on non-punished responding.

| Treatment | Dose (mg/kg) | Response Rate (% of control ± s.e.) |
|---|---|---|
| Caramiphen | 14.0 | 74.0 ± 10.4 |
|  | 28.0 | 44.0 ± 9.2[a] |
| Physostigmine + Caramiphen | 0.1 28.0 | 63.3 ± 9.5[a,b] |
| Diphenylhydantoin | 8.1 | 117.6 ± 11.4 |
|  | 16.2 | 108.9 ± 5.2 |
| Atropine | 30.0 | 25.4 ± 10.7[a] |
| Physostigmine | 0.1 | 69.4 ± 8.5[a] |
| Physostigmine + Atropine | 0.1 30.0 | 42.3 ± 6.9[a,b] |

[a]Significantly different from control (p = 0.05. Student's t-test).
[b]Significantly different from corresponding pretreatment group (p = 0.05. Student's t-test).

TABLE V

| The effect of Atropine on MES convulsions. | | |
|---|---|---|
| Atropine (mg/kg) | Duration of TFE (sec ± s.e.) | % Responding (THE) |
| 0 | 12.5 = 0.4 | 90 |
| 25 | 13.4 = 0.4 | 90 |
| 50 | 13.5 = 0.4 | 70 |
| 75 | 13.1 = 0.4 | 70 |
| 150 | 13.8 = 0.5 | 50 |
| 300 | 12.1 = 0.2 | 70 |

What is claimed is:

1. A composition comprising an effective amount for controlling seizures in a mammal of a combination of an anti-epileptic hydantoin and a compound selected from the group consisting of opipramol and benztropine, wherein the amount of said compound is at least sufficient to potentiate said hydantoin.

2. The composition of claim 1 wherein the amount of said hydantoin is substantially lower than that which would display the same seizure-controlling activity if said hydantoin had been used as the sole active ingredient.

3. The composition of claim 2 wherein said hydantoin is diphenylhydantoin.

4. The composition of claim 3 wherein said compound is benztropine.

5. The composition of claim 3 wherein said compound is opipramol.

6. The composition of claim 2 wherein said compound is used at a subthreshold level.

7. The composition of claims 1, 4 or 5 contained in a liquid injectable dosage form.

8. The composition of claims 1, 4 or 5 contained in a solid oral dosage form.

9. The composition of claims 1, 4 or 5 contained in a liquid oral dosage form.

10. A method for controlling seizures in a mammal in need of such treatment comprising administering to said mammal an amount of
    (a) an anti-epileptic hydantoin; and
    (b) an anti-epileptic hydantoin-potentiating amount of a compound selected from the group consisting of benztropine and opipramol; said amounts in combination being effective for controlling seizures in said mammal.

11. The method of claim 10 wherein said hydantoin is diphenylhydantoin.

12. The method of claim 11 wherein said amount of said phenylhydantoin is substantially lower than that which would display the same seizure-controlling activity if diphenylhydantoin alone had been administered.

13. The method of claim 11 wherein the amount of said compound is sufficient to potentiate with hydantoin.

14. The method of claim 11 wherein said diphenylhydantoin and said compound are co-administered.

15. The method of claim 11 wherein said diphenylhydantoin and said compound are administered successively.

* * * * *